United States Patent
St. John et al.

(10) Patent No.: US 11,426,408 B2
(45) Date of Patent: Aug. 30, 2022

(54) USE OF SEROTONERGIC DRUGS TO TREAT VIRUS-INDUCED THROMBOCYTOPENIA

(71) Applicant: NATIONAL UNIVERSITY OF SINGAPORE, Singapore (SG)

(72) Inventors: Ashley Lauren St. John, Singapore (SG); Mohamad Fadhli Bin Masri, Singapore (SG); Abhay Rathore, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/760,318

(22) PCT Filed: Oct. 31, 2018

(86) PCT No.: PCT/SG2018/050552
§ 371 (c)(1),
(2) Date: Apr. 29, 2020

(87) PCT Pub. No.: WO2019/088926
PCT Pub. Date: May 9, 2019

(65) Prior Publication Data
US 2020/0352947 A1   Nov. 12, 2020

(30) Foreign Application Priority Data
Nov. 1, 2017 (SG) .............................. 10201709025P

(51) Int. Cl.
| | |
|---|---|
| *A61K 31/517* | (2006.01) |
| *A61P 31/14* | (2006.01) |
| *A61K 31/138* | (2006.01) |
| *A61K 31/225* | (2006.01) |
| *A61K 31/343* | (2006.01) |
| *A61K 31/4525* | (2006.01) |
| *A61K 31/497* | (2006.01) |

(52) U.S. Cl.
CPC .......... *A61K 31/517* (2013.01); *A61K 31/138* (2013.01); *A61K 31/225* (2013.01); *A61K 31/343* (2013.01); *A61K 31/4525* (2013.01); *A61K 31/497* (2013.01); *A61P 31/14* (2018.01)

(58) Field of Classification Search
None
See application file for complete search history.

(56) References Cited

U.S. PATENT DOCUMENTS 9,730,921 B2 * 8/2017 Abraham ............. G01N 33/573
10,668,059 B2 * 6/2020 Abraham ............. A61K 31/352

FOREIGN PATENT DOCUMENTS

WO         96/01107 A1    1/1996
WO    WO2013/148366 A1   10/2013

OTHER PUBLICATIONS

Nukuzuma et al., "Inhibitory effect of serotonin antagonists on JC viruspropagation in a carrier culture of humanneuroblastoma cells", 2009, Microbiology and Immunology, 53(9), pp. 496-501. (Year: 2009).*
Jahnke et al., "An evaluation of intravenous immunoglobulin in the treatment of human immunodeficiency virus-associated thrombocytopenia", 1994, TRANSFUSION, 34(9), pp. 759-764. (Year: 1994).*
Nachman et al., "Platelets, Petechiae, and Preservation of the Vascular Wall", 2008, The New England Journal of Medicine, 359(12), pp. 1261-1270. (Year: 2008).*
International Search Report dated Dec. 11, 2018 corresponding to PCT/SG2018/050552 filed Oct. 31, 2018; 6 pages.
Written Opinion of the International Searching Authority dated Dec. 11, 2018 corresponding to PCT/SG2018/050552 filed Oct. 31, 2018; 7 pages.
Assinger Alice et al., "Platelets and infection—an emerging role of platelets in viral infection," *Frontiers in Immunology* (Dec. 18, 2014) 5:649.
Cheng, Han et al., "Inhibition of Ebola and Marbur virus entry by G protein-coupled receptor antagonists," *Journal of Virology* (Sep. 1, 2015) 89(19):9932-9938.
Cloutier, Nathalie et al., Platelets can enhance vascular permeability, *Blood* (Aug. 9, 2012) 120(6):1334-1343.
Lang, Philipp A. et al., "Aggravation of viral hepatitis by platelet-derived serotonin," *Nature Medicine* (May 30, 2008) 14(7):756-761.
Morrison, Juliet et al., "Transcriptional Profiling Confirms the Therapeutic Effects of Mast Cell Stabilization in a Dengue Disease Model," *Journal of Virology* (Aug. 24, 2017) 91(18):e00617-17.
St. John, Ashley L. et al., "Contributions of mast cells and vasoactive products, leukotrienes and chymase, to dengue virus-induced vascular leakage," *ELife* (Apr. 30, 2013) 2:e00481.
Syenina, Ayesa et al., "Dengue vascular leakage is augmented by mast cell degranulation mediated by immunoglobulin Fc gamma receptors," *ELife* (Mar. 18, 2015); 4:e05291 (16 pages).
Walther, Diego J. et al., "Serotonylation of Small GTPases is a Signal Transduction Pathway that Triggers Platelet α-Granule Release," *Cell* (Dec. 24, 2003) 115(7):851-862.

(Continued)

*Primary Examiner* — My-Chau T. Tran
(74) *Attorney, Agent, or Firm* — Mintz, Levin, Cohn, Ferris, Glovsky and Popeo, P.C.

(57) ABSTRACT

The present invention relates to the use of serotonergic compounds for the treatment of virus-induced thrombocytopenia. More particularly, the invention relates to methods of treating thrombocytopenia by blocking serotonin activity. For example, inhibitors of receptor 5HT2A and/or receptor 5HT1A and/or inhibitors of mast cell degranulation and/or inhibitors of serotonin uptake may be used. Preferably, the thrombocytopenia is induced by dengue or Japanese Encephalitis virus, and the inhibitors are preferably ketanserin, WAY-100135, sarpogrelate, or fluoxetine.

15 Claims, 10 Drawing Sheets

(56) References Cited

OTHER PUBLICATIONS

Duane J. Gubler, "Dengue and Dengue Hemorrhagic Fever", Clinical Microbiology Reviews, vol. 11, No. 3, Jul. 1998, pp. 480-496.
Maria G. Guzman & Eva Harris, "Dengue", www.thelancet.com, vol. 385, Jan. 31, 2015, 315, pp. 453-465.
Scott B. Halstead, "Dengue", www.thelancet.com, vol. 370, Nov. 10, 2007, pp. 1644-1652.
Eugenio D. Hottz, et al., :Platelet Activation and Apoptosis Modulate Monocyte Inflammatory Responses in Dengue, The Journal of Immunology, http://www.jimmunol.org/content/193/4/1864, Jul. 2014, pp. 1864-1872.
Deborah M. Kurrasch-Orbaugh, et al., "A complex signaling cascade links the serotonin2A receptor to phospholipase A2 activation: the involvement of MAP kinases", Journal of Neurochemistry, vol. 86, 2003, pp. 980-991.
Jonas D. Albarnaz, et al., "MEK/ERK activation plays a decisive role in yellow fever virus replication: Implication as an antiviral therapeutic target", Antiviral Research 111, 2014, pp. 82-92.
Alice Assinger, "Platelets and infection—an emerging role of platelets in viral infection", www.frontiersin.org, vol. 5, Article 649, Dec. 2014, pp. 1-12.
Claude R. Benedict, et al., "Correlation of Plasma Serotonin Changes with Platelet Aggregation in an in Vivo Dog Model of Spontaneous Occlusive Coronary Thrombus Formation", Circulation Research/ vol. 58, No. 1, Jan. 1986, pp. 58-67.
F. Cerrito, et al., "$5HT_2$-Receptors and Serotonin Release: Their Role In Human Platelet Aggregation", Life Sciences, vol. 53, Apr. 29, 1993, pp. 209-215.
Fred F. De Clerck and Arnold G. Herman, "5-Hydroxytryptamine and platelet aggregation", Federation Proceedings, vol. 42, No. 2, Feb. 1983, pp. 228-232.
Fred De Clerck, Jean-Louis David & Paul A.J. Janssen, "Inhibition of 5-hydroxytryptamine-induced and -amplified human platelet aggregation by ketanserin (R 41 468), a selective 5-HT2-receptor antagonist", Agents and Actions, vol. 12, No. 3, 1982, pp. 388-397.
R. Elizabeth Gregory and David S. Ettinger, "$5-HT_3$ Receptor Antagonists for the Prevention of Chemotherapy-Induced Nausea and Vomiting A Comparison of Their Pharmacology and Clinical Efficacy", *Gregory & Ettinger*, Adis International Limited, vol. 55, No. 2, Feb. 1998, pp. 173-189.
Ashley L. St. John, Soman N. Abraham and Duane J. Gubler, "Barriers to preclinical investigations of anti-dengue immunity and dengue pathogenesis", PERSPECTIVES, www.nature.com/reviews/ micro, vol. 11, Jun. 2013, pp. 420-426.
Ashley L St John, et al., "Contributions of mast cells and vasoactive products, leukotrienes and chymase, to dengue virus-induced vascular leakage", St John et al. eLife, Apr. 30, 2013, pp. 1-18.
Ayesa Syenina, et al., "Dengue vascular leakage is augmented by mast cell degranulation mediated by immunoglobulin Fcγ receptors", Syenina et al. eLife Mar. 18, 2015, pp. 1-16.
Diego J. Walther, et al., "Serotonylation of Small GTPases Is a Signal Transduction Pathway that TriggersPlatelet α-Granule Release", Cell Press, vol. 115, Dec. 26, 2003, pp. 851-862.
Robert Langer, "New Methods of Drug Delivery", SCIENCE, vol. 249, Sep. 28, 1990, pp. 1527-1533.
Chong Liu, et al., "Effects of Ketanserin on Endotoxic Shock and Baroreflex Function in Rodents", Anti-Shock Effect of Ketanserin JID 2011:204, Nov. 15, 15, 2011, pp. 1605-1612.
Chong Liu, et al., "The protective action of ketanserin against lipopolysaccharide-induced shock in mice is mediated by inhibiting inducible NO synthase expression via the MEK/ERK pathway", Free Radical Biology and Medicine vol. 65, 2013, pp. 658-666.
William I. Rosenblum, M.D., and Farouk El-Sabban, Ph.D., "Dimethyl Sulfoxide (DMSO) and Glycerol, Hydroxyl Radical Scavengers, Impair Platelet Aggregation Within and Eliminate the Accompanying Vasodilation of, Injured Mouse Pial Arterioles", Reversible Cerebral Ischemia, Stroke, vol. 13, No. 1, Jan.-Feb. 1982, pp. 35-39.
A. Sjoerdsma, et al., "Serotonin and Histamine in Mast Cells", American Association for the Advancement of Science, vol. 125, Jun. 14, 1957, pp. 1202-1203.
Omer Iqbal, et al., "Selective Serotonin Reuptake Inhibitors Influence Agonist-Induced Platelet Aggregation. Preliminary Results from Comorbidity of Depression and Cardiovascular Disease Study", https://ashpublications.org/blood/article/112/11/4556/62367/Selective-Serotonin-Reuptake-Inhibitors-Influence, Blood, vol. 112, No. 11, 2008, 2 pgs.

\* cited by examiner

USE OF SEROTONERGIC DRUGS TO TREAT VIRUS-INDUCED THROMBOCYTOPENIA

FIELD OF THE INVENTION

The present invention relates to treatment of virus-induced thrombocytopenia. More particularly, the invention relates to methods of treating thrombocytopenia by blocking serotonin activity. For example, inhibitors of receptor 5HT2A and/or receptor 5HT1A and/or inhibitors of mast cell degranulation and/or inhibitors of serotonin uptake may be used.

BACKGROUND

Dengue fever is caused by infection with dengue virus, of which there are four serotypes. There are no targeted therapies available to treat dengue infection or its characteristic symptoms such as thrombocytopenia or hemorrhage. Current measures involve symptomatic treatment, as well as vaccination. Some communities, such as Singapore, engage in vector control to prevent further spread of disease [Guzman, M. G. & Harris, E. Dengue. *The Lancet* 385, 453-465 (2015)], but the results of vector control have been limited. Although dengue fever usually resolves on its own, there is a possibility of severe complications, such as dengue hemorrhagic fever and dengue shock syndrome (DHF/DSS). Patients with DHF/DSS frequently experience substantially decreased platelet counts, abdominal pain and plasma leakage that can lead to organ damage and/or shock [St John, A. L., et al., *Nature reviews. Microbiology* 11, 420-426 (2013)]. Due to this possibility, patients can be admitted to hospitals for monitoring. Reduced platelet count, or thrombocytopenia, is one of the most consistent symptoms of dengue disease and this frequently occurs in patients diagnosed with both mild and severe forms of dengue infection [St John, A. L., et al., *Nature reviews. Microbiology* 11, 420-426 (2013); Halstead, S. B. *Lancet* 370, 1644-1652 (2007)]. This can predispose the patient to severe bleeding, which can be fatal. In addition to dengue, many viruses induce thrombocytopenia, including human immunodeficiency virus, hepatitis C, Bunyaviruses, rotavirus, hantavirus, adenoviruses, Epstein-Barr virus, cytomegalovirus and others [Assinger, A. *Frontiers in immunology* 5, 649 (2014)].

Current estimates suggest that 390 million people are infected with dengue virus each year [de Clerck. F., et al., *Agents Actions* 43, 225-234 (1994)]. There is a high burden clinically and economically due to the need for admissions during severe infection. Hence, any treatment for dengue fever would represent a significant benefit for both patients and healthcare providers.

Previous studies have shown that production of inflammatory mediators (including those made by mast cells) and platelet activation are important features of dengue pathogenesis. There is a need to provide treatments that alleviate virus-induced thrombocytopenia.

SUMMARY OF THE INVENTION

It has surprisingly been found that the activation of mast cells by virus infection leads to release of serotonin into the circulation, leading to platelet activation and aggregation and thrombocytopenia. Administration of serotonergic drugs prevented or ameliorated the development of thrombocytopenia in vivo.

Drugs targeting serotonin or preventing its release can be used to treat virus induced thrombocytopenia. Targeting the serotonin receptor 5HT2A and/or 5HT1A using receptor antagonists, or preventing the uptake of serotonin into platelets prevents virus-induced thrombocytopenia and blocks platelet aggregation, Serotonin inhibitors represent a novel treatment strategy for dengue virus (DENV), Japanese encephalitis virus (JEV) and perhaps other viruses that induce thrombocytopenia and downstream complications such as human immunodeficiency virus (HIV), hepatitis C (HCV), bunyaviruses, rotavirus, hantavirus, adenoviruses (ADV), Epstein-Barr virus (EBV) and cytomegalovirus (CMV). Many serotonergic drugs, in particular ketanserin, have been approved for use. Hence, costly and time-consuming safety trials can be by-passed, permitting faster clinical usage. By preventing thrombocytopenia, the severity of infection can be reduced, leading to fewer medical complications and fewer hospital admissions [St John, et al., *Nature reviews Microbiology* 11, 420-426 (2013)]. This represents a large medical and economic benefit.

According to a first aspect, the present invention provides a composition comprising at least one serotonergic compound for treating virus-induced thrombocytopenia.

In preferred embodiments, the at least one serotonergic compound inhibits serotonin release from mast cells and/or serotonin uptake by platelets and/or inhibits serotonin activity. Serotonin release from mast cells may be inhibited by 5HT1A receptor antagonists or by mast cell stabilizers that inhibit degranulation, Mast cell stabilizers might have a benefit of preventing the release of serotonin, but would not be able to block the effects of already released serotonin. Serotonin uptake by platelets may be inhibited by selective serotonin uptake inhibitors (SSRIs) or serotonin antagonist and reuptake inhibitors (SARIs), whereas inhibition of activity of serotonin on platelets may be effected using 5HT2A receptor antagonists, ERK pathway inhibitors or serotonylation inhibitors.

Thus, in preferred embodiments the at least one serotonergic compound is selected from one or more of the group comprising serotonin 5HT2A receptor antagonists, serotonin 5HT1A receptor antagonists, SSRIs, SARIs, ERK pathway inhibitors and mast cell stabilizers.

In more preferred embodiments the at least one serotonergic compound is at least one serotonin 5HT2A receptor antagonist and/or at least one serotonin 5HT1A receptor antagonist.

In some embodiments, the composition of any aspect of the invention comprises pharmaceutically acceptable salts or solvates, or pharmaceutically functional derivatives of said at least one serotonergic compound.

According to another aspect, the present invention provides use of at least one serotonergic compound, or pharmaceutically acceptable salt or solvate thereof, for the manufacture of a medicament for treating virus-induced thrombocytopenia.

In preferred embodiments the at least one serotonergic compound, or pharmaceutically acceptable salt or solvate thereof, inhibits serotonin release and/or inhibits serotonin activity.

In more preferred embodiments the medicament comprises one or more serotonergic compounds, or pharmaceutically acceptable salt or solvate thereof, selected from the group comprising serotonin 5HT2A receptor antagonists, serotonin 5HT1A receptor antagonists, ERK pathway inhibitors and mast cell stabilizers.

In more preferred embodiments the medicament comprises at least one serotonin 5HT2A receptor antagonist and/or at least one serotonin 5HT1A receptor antagonist.

In more preferred embodiments according to any aspect of the invention, the at least one serotonergic compound is selected from one or more from the group comprising:
5HT2A receptor inhibitor as;
ketanserin [3-[2-[4-(4-fluorobenzoyl)piperidin-1-yl]ethyl]-1H-quinazoline-2,4-dione], sarpogrelate [4-[1-(dimethylamino)-3-[2-[2-(3-methoxyphenyl)ethyl]phenoxy]propan-2-yl]oxy-4-oxobutanoic acid],
ritanserin [6-[2-[4-[bis(4-fluorophenyl)methylidene]piperidin-1-yl]ethyl]-7-methyl-[1,3]thiazolo[3,2-a]pyrimidin-5-one],
fananserin [2-(3-(4-(4-fluorophenyl)-1-piperazinyl)propyl)-2H-naphth(1,8-cd)isothiazole 1,1-dioxide] or
antipsychotics, such as
risperidone [3-[2-[4-(6-fluoro-1,2-benzoxazol-3-yl)piperidin-1-yl]ethyl]-2-methyl-6,7,8,9-tetrahydropyrido[1,2-a]pyrimidin-4-one] or
quetiapine [2-[2-(4-benzo[b][1,4]benzothiazepin-6-ylpiperazin-1-yl)ethoxy]ethanol]; 5HT1A receptor inhibitors such as
WAY 100135 [(S)—N-tert-butyl-3-(4-(2-methoxyphenyl)-piperazin-1-yl)-2-phenylpropanamide],
methiothepin [1-methyl-4-ethylsulfanyl-5,6-dihydrobenzo[b][1]benzothiepin-5-yl)piperazine],
pindolol [1-(1H-indol-4-yloxy)-3-(propan-2-ylamino)propan-2-ol],
dotarizine [1-(Diphenylmethyl)-4-[3-(2-phenyl-1,3-dioxolan-2-yl)propyl]piperazine] and flopropione [1-(2,4,6-Trihydroxyphenyl)-1-propanone];
ERK pathway inhibitors such as
SCH772984 [(3R)-1-[2-oxo-2-[4-(4-pyrimidin-2-ylphenyl)piperazin-1-yl]ethyl]-N-(3-pyridin-4-yl-1H-indazol-5-yl)pyrrolidine-3-carboxamide] and
VTX11e [4-[2-(2-chloro-4-fluoroanilino)-5-methylpyrimidin-4-yl]-N-[(1S)-1-(3-chlorophenyl)-2-hydroxyethyl]-1H-pyrrole-2-carboxamide];
mast cell stabilizers such as
cromolyn [5-[3-(2-carboxy-4-oxochromen-5-yl)oxy-2-hydroxypropoxy]-4-oxochromene-2-carboxylic acid] and
ketotifen [10-(1-methylpiperidin-4-ylidene)-5H-benzo[1,2]cyclohepta[3,4-b]thiophen-4-one];
serotonylation inhibitors such as cystamine;
selective serotonin uptake inhibitors (SSRIs) or serotonin antagonist and reuptake inhibitors (SARIs) such as fluoxetine, paroxetine, citalopram, etoperidone and, lorpiprazole,
or pharmaceutically acceptable salt or solvate thereof.

In more preferred embodiments according to any aspect of the invention, the at least one serotonergic compound is selected from the group comprising:
ketanserin [3-[2-[4-(4-fluorobenzoyl)piperidin-1-yl]ethyl]-1H-quinazoline-2,4-dione], sarpogrelate [4-[1-(dimethylamino)-3-[2-[2-(3-methoxyphenyl)ethyl]phenoxy]propan-2-yl]oxy-4-oxobutanoic acid] and
WAY 100135 [(S)—N-tert-butyl-3-(4-(2-methoxyphenyl)-piperazin-1-yl)-2-phenylpropanamide], or pharmaceutically acceptable salt or solvate thereof.

According to another aspect, the present invention provides a method of treatment of virus-induced thrombocytopenia, comprising administering to a subject in need thereof an efficacious amount of a composition according to any aspect of the invention.

In preferred embodiments the subject is administered at least one serotonin 5HT2A receptor antagonist and/or at least one serotonin 5HT1A receptor antagonist. Suitable routes of administration would be understood by those skilled in the art.

In preferred embodiments the composition is administered intravenously, orally, sublingually or intraperitoneally.

According to any aspect of the present invention the thrombocytopenia-causing virus is selected from the group comprising a flavivirus, such as dengue virus or Japanese encephalitis virus; human immunodeficiency virus, hepatitis C, Bunyaviruses, rotavirus, hantavirus, adenoviruses, Epstein-Barr virus and cytomegalovirus.

In preferred embodiments the virus is a flavivirus, such as dengue virus or Japanese encephalitis virus.

(A) Whole blood from healthy human volunteers was isolated and stimulated with DENV2, serotonin, or DENV2+ serotonin for 15 min. Cells were then fixed and stained for platelet markers CD41 and CD62P and analyzed by flow cytometry. DENV raised the activation levels of platelets. DENV in the presence of serotonin significantly enhanced platelet activation over control and DENV groups (n=4). (B) Human whole blood was stimulated with DENV2, mast cells (MCs) or DENV2+MCs in the presence of vehicle or ketanserin (100 nM or 500 nM) for 15 min prior to assessment of platelet activation. Ketanserin treatment abolished the significant increase in platelet activation that occurred in the DENV2+MC treated group compared to controls (n=4). Mean values are presented and error bars represent the SEM. P values were determined by one-way ANOVA; *P<0.05, P<0.01, *P<0.001, ****P<0.0001, ns: non-significant.

Figure 10:
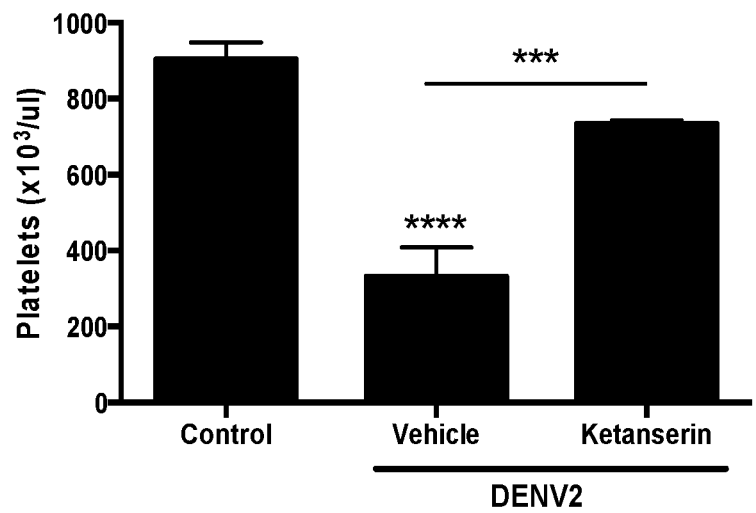

FIG. 10 shows that ketanserin treatment prevents thrombocytopenia. Platelet counts of DENV2 infected mice. Mice were infected via intraperitoneal route (IP) with 10$^6$ plaque forming units (pfu) and were given either vehicle (1% DMSO) or ketanserin 8 mg/kg IP. Blood was taken via cheek bleed 24 hours post-infection and platelet counts were measured using an automated hematology analyzer. DENV2 infection induces thrombocytopenia, but ketanserin treatment is able to prevent thrombocytopenia (n=5). Mean values are presented and error bars represent the SEM. P values were determined by Student's unpaired t test; *P<0.001, **P<0.0001.

Figure 11:
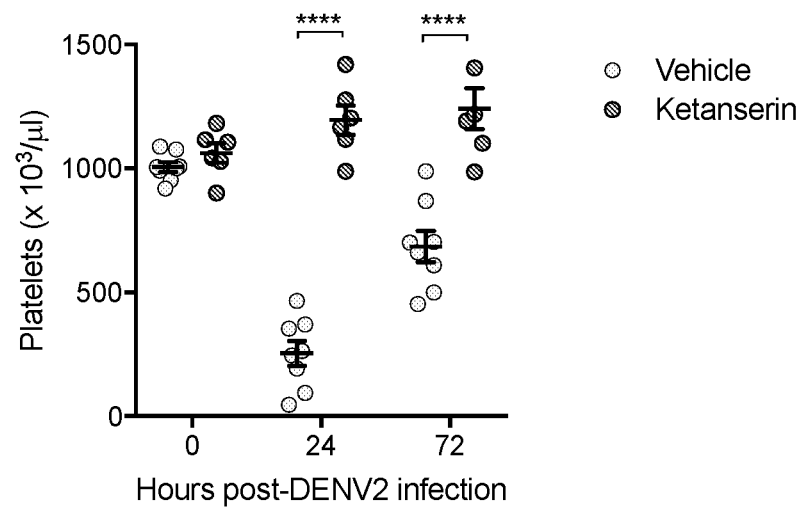

FIG. 11 shows that ketanserin treatment prevents thrombocytopenia in an alternative mouse model of DENV infection. Platelet counts of DENV2 infected mice. Mice deficient in interferon signalling (IFNαβγ-KO) were infected via intraperitoneal route (IP) with 10$^6$ plaque forming units (pfu) and were given either vehicle (1% DMSO) or ketanserin 8 mg/kg P. Blood was taken via cheek bleed 24 and 72 hours post-infection and platelet counts were measured using an automated hematology analyzer. DENV2 infection induced thrombocytopenia, but ketanserin treatment was able to prevent thrombocytopenia (n=5). Mean values are presented and error bars represent the SEM. P values were determined by Student's unpaired t test; ****P<0.0001.

Figure 12:
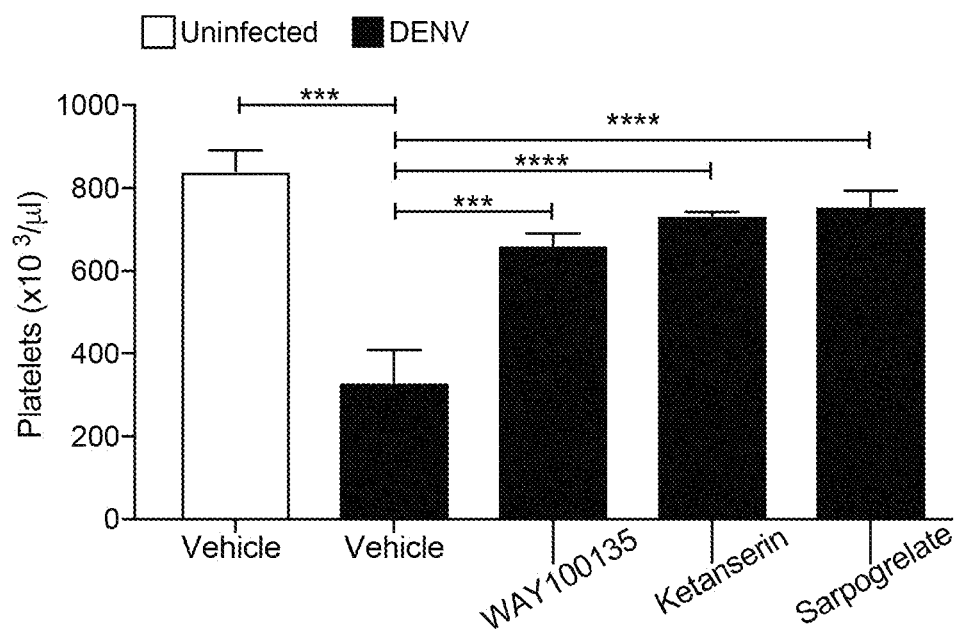

FIG. 12 shows that targeting serotonin receptors prevents thrombocytopenia. Platelet counts of DENV2 infected mice. Mice were infected IP with 10$^6$ pfu of DENV2 and were given either vehicle, the 5HT1A antagonist WAY-100135, or either of the 5HT2A antagonists, ketanserin and sarpogrelate. Blood was taken via cheek bleed 24 hours post-infection and platelet counts were measured using an automated hematology analyzer. DENV2 infection induced thrombocytopenia that was able to be prevented through administration of serotonin receptor antagonists (n=5). Mean values are presented and error bars represent the SEM. P values were determined by one-way ANOVA; *p<0.001, **P<0.0001.

Figure 13:
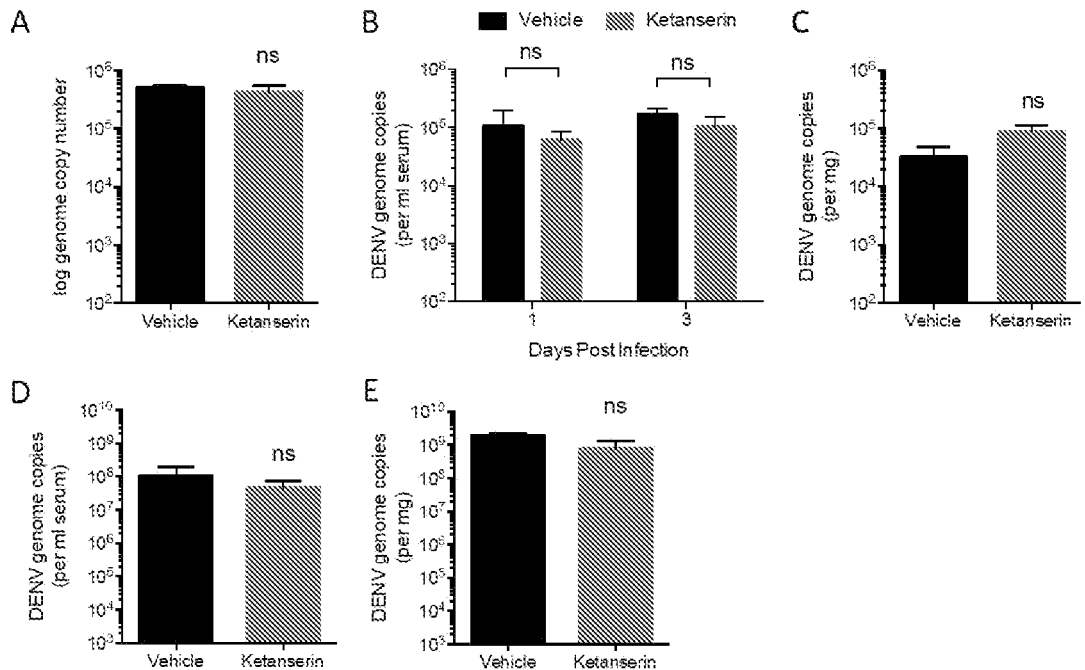

FIG. 13 shows targeting 5HT$_{2A}$ receptors does not affect viremia during DENV infection. (A) WT mice were treated with vehicle or ketanserin (8 mg/kg) prior to subcutaneous footpad injection with 2×10$^5$ pfu of DENV or PBS. At 72 h post-infection, popliteal lymph nodes were isolated for viral quantification by qRT-PCR. Ketanserin treatment did not affect viral load in the draining lymph node. (B-C) WT mice were infected with DENV2 (1×10$^6$ pfu, i.p.) and treated daily with either 8 mg/kg of ketanserin or vehicle. (B) At indicated days, serum was isolated for viral quantification by qRT-PCR which showed no difference in viremia (n=5 per group). (C) At 1 day post-infection, the spleen was harvested and DENV2 was quantified by qRT-PCR. Ketanserin treatment did not affect viral load in the spleen. (D-E) (IFN-α, β,γ-R$^{-/-}$ (IFNR-KO) mice were infected with DENV2 (2×10$^5$ pfu, i.p.) and treated daily with either 8 mg/kg of ketanserin or vehicle. Serum (D) and spleen (E) was isolated for viral quantification via qRT-PCR 72 h post-infection, and showed no difference in viremia. Mean values are presented and error bars represent the SEM (n=4-5 per group). P values were determined by Student's unpaired t test; ns: non-significant.

Figure 14:
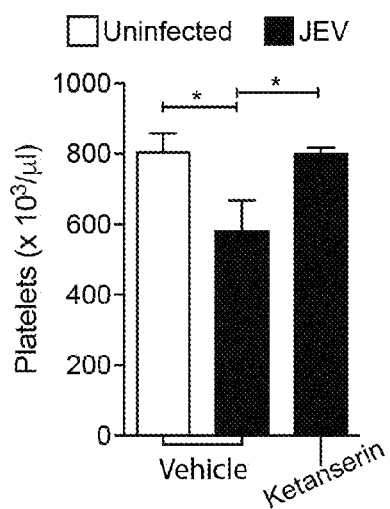

FIG. 14 shows that ketanserin reduces JEV induced thrombocytopenia. Platelet counts of JEV infected mice. Mice were infected with 10$^6$ pfu of JEV intraperitoneally and were vehicle- or ketanserin-treated (8 mg/kg) at 1 hour post-infection. At 24 hours, blood was collected and platelet counts were measured. The drop in platelet counts induced by JEV was prevented by ketanserin treatment (n=5). Mean values are presented and error bars represent the SEM. P values were determined by Student's unpaired t test; *p<0.05.

Figure 15:
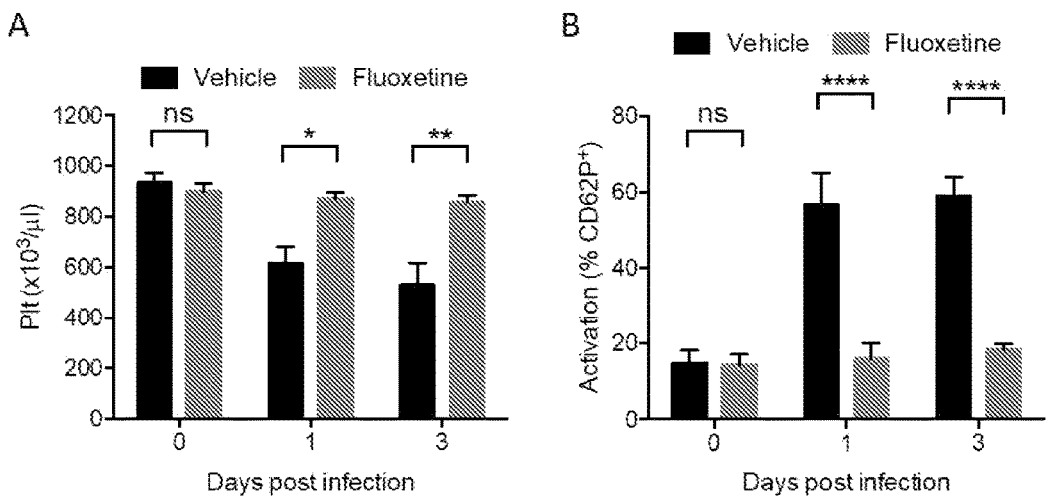

FIG. 15 shows that fluoxetine reduces DENV induced thrombocytopenia. Mice were administered fluoxetine (20 mg/kg/day) or vehicle via drinking water for 2 weeks. Mice were then infected with 10$^6$ pfu of DENV2 intraperitoneally. At 24 and 72 hours, blood was collected and platelet counts were measured. The reduction in platelet counts and increased platelet activation induced by DENV was prevented by fluoxetine treatment (n=5). Mean values are presented and error bars represent the SEM. P values were determined by one-way ANOVA; *P<0.05, P<0.01, *P<0.001, ****P<0.0001.

Figure 16:
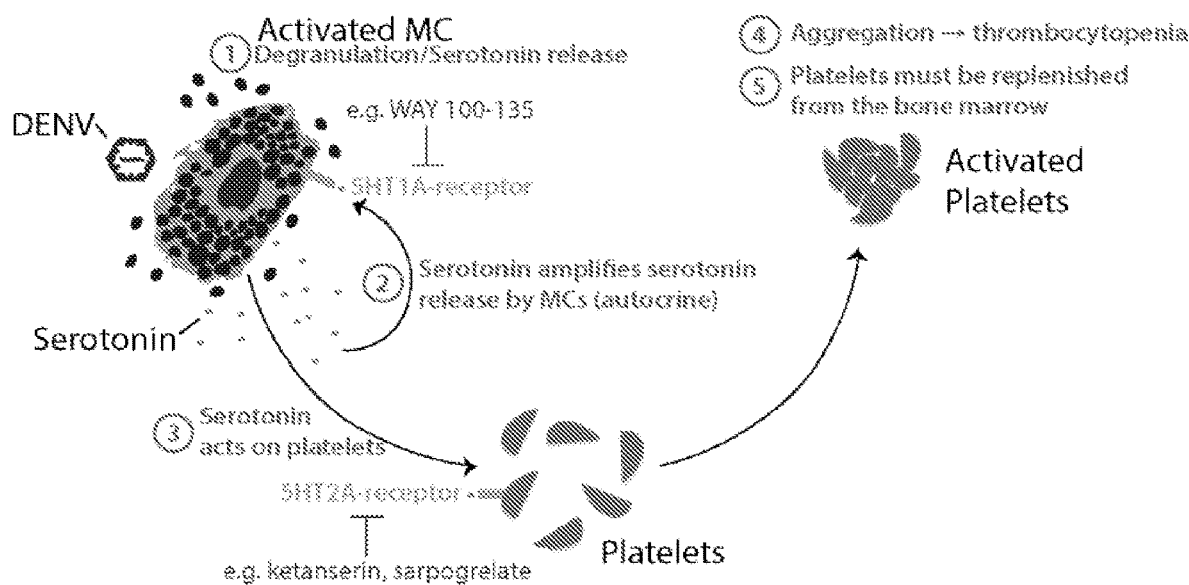

FIG. 16. Shows a schematic diagram of the targets of the invention. DENV activates mast cells, resulting in degranulation of mast cells, leading to the release of serotonin. Serotonin acts on mast cells via 5-HT1A receptors in an autocrine manner, further increasing release of mast cell derived products. Serotonin acts on platelets via the 5HT2A receptor, leading to platelet aggregation and subsequently thrombocytopenia which is restored during recovery as new platelets are released from the bone marrow. Possible pharmacological inhibitors of these receptors are shown.

DETAILED DESCRIPTION OF THE INVENTION

Bibliographic references mentioned in the present specification are for convenience listed in the form of a list of references and added at the end of the examples. The whole content of such bibliographic references is herein incorporated by reference.

Definitions

Certain terms employed in the specification, examples and appended claims are collected here for convenience.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

As used herein, the term "serotonergic compound" is to be broadly interpreted as a compound that is any chemical that modifies the effects of serotonin in the body by modulating production, destruction, reuptake, release, receptor antagonists etc. More particularly, the term encompasses compounds that inhibit the effect of serotonin on platelet number following virus infection. Serotonergic compounds according to the invention include those which inhibit the serotonin receptor 5HT2A and/or 5HT1A, inhibit the ERK pathway downstream of serotonin activation, or inhibit mast cell degranulation thereby inhibiting release of serotonin and its effect on platelet numbers. Examples of serotonergic compounds include 5HT2A receptor inhibitors such as ketanserin, sarpogrelate, ritanserin, fananserin or antipsychotics, such as risperidone or quetiapine; 5HT1A receptor inhibitors such as WAY 100135, methiothepin, pindolol, dotarizine and flopropione; ERK pathway inhibitors such as SCH772984 and VTX11e; mast cell stabilizers such as cromolyn and ketotifen; serotonylation inhibitors such as cystamine; selective serotonin uptake inhibitors (SSRIs) or serotonin antagonist and reuptake inhibitors (SARIs) such as fluoxetine, paroxetine, citalopram, etoperidone and lorpiprazole.

References herein (in any aspect or embodiment of the invention) to said serotonergic compounds includes references to such compounds per se, to tautomers of such compounds, as well as to pharmaceutically acceptable salts or solvates, or pharmaceutically functional derivatives of such compounds.

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a serotonergic compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by serotonergic compounds are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallizing the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

The term "antagonist", or "inhibitor" as it is used herein, refers to a molecule which decreases the amount or the duration of the effect of the biological activity of serotonin, Antagonists may include proteins, nucleic acids, carbohydrates, antibodies, or small molecules which decrease the effect of serotonin. For example, an antagonist may be used according to the invention to inhibit the serotonin receptor 5HT2A and/or 5HT1A. An antagonist may be used according to the invention to inhibit mast cell degranulation, thereby inhibiting release of serotonin and its effect on platelet numbers.

Compounds of the present invention will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington The Science and Practice of Pharmacy, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, Science (1990) 249, 1527.

Otherwise, the preparation of suitable formulations may be achieved routinely by the skilled person using routine techniques and/or in accordance with standard and/or accepted pharmaceutical practice.

The amount of a compound in any pharmaceutical formulation used in accordance with the present invention will depend on various factors, such as the severity of the condition to be treated, the particular patient to be treated, as well as the compound(s) which is/are employed. In any event, the amount of a compound in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Dengue Infection Induces Platelet Aggregation in Mice

Figure 1:
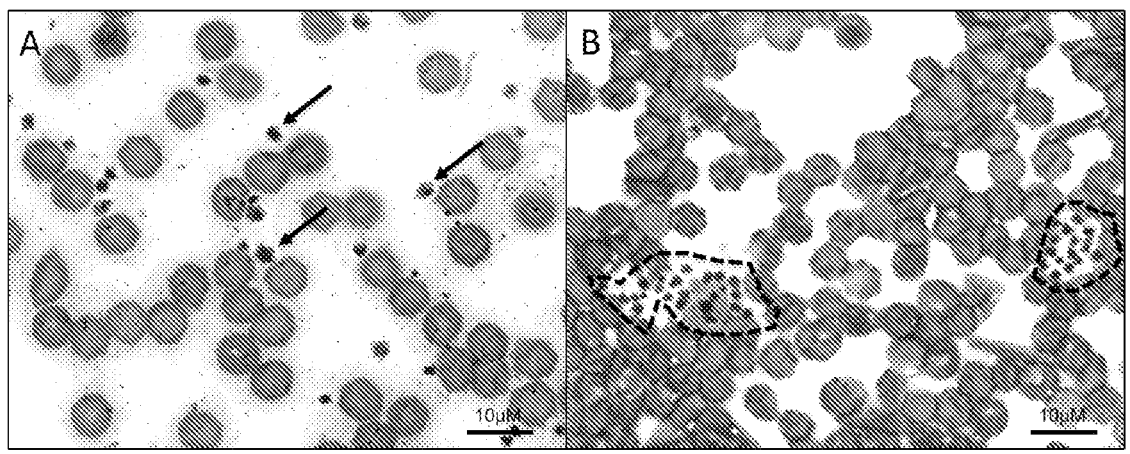
FIG. 1 shows that Dengue induces platelet aggregation. The images depict peripheral blood smears from DENV2-infected mice. Mice were infected via the intraperitoneal route (IP). Blood was taken via cheek bleed 24 hours post-infection, smeared onto a glass slide, stained with eosin and methylene blue and viewed under light microscopy. (A) Mock infected mice. A few individual platelets are denoted with arrows (B) DENV infected mice. Platelet aggregates are circled by dashed lines. Scale bar=10 μm.

Wild type (WT) mice were infected via the intraperitoneal route (IP) with $10^6$ plaque forming units (pfu) of DENV2. Blood was taken via cheek bleed 24 hours post-infection, smeared onto a glass slide, stained with eosin and methylene blue and viewed under light microscopy using a 100× magnification lens. The peripheral blood smears of infected mice revealed substantial aggregation of platelets (FIG. 1).

Example 2

Figure 2:
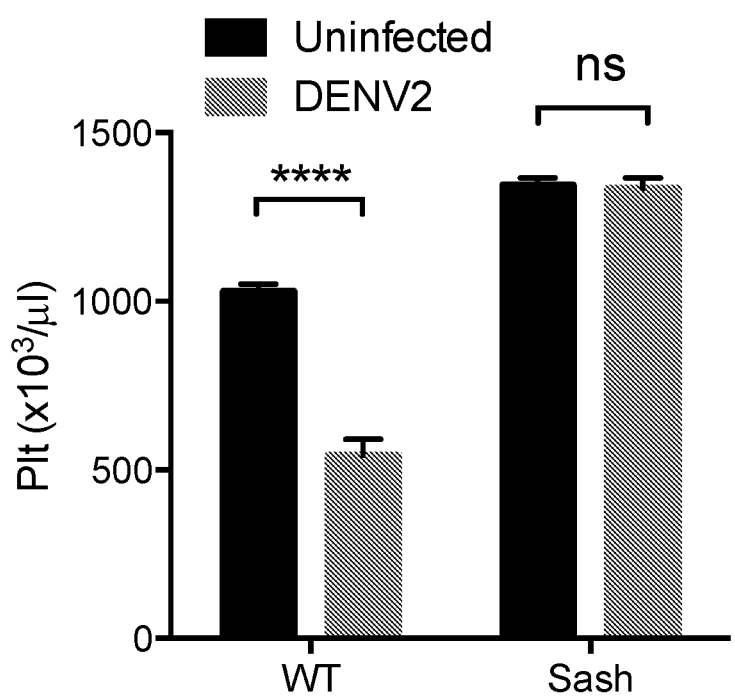
FIG. 2 shows that mice lacking mast cells do not experience thrombocytopenia during dengue infection. Platelet counts in DENV-infected wild type (WT) and mast cell-deficient (Sash) mice. Mice were infected via intraperitoneal route (IP) with $10^6$ plaque forming units (pfu). Blood was taken via cheek bleed 24 hours post-infection and platelet counts were measured using an automated hematology analyzer. Dengue virus infection results in thrombocytopenia in wild type mice, but not in mast cell-deficient mice (n=9-15 per group). Means are presented with error bars representing the SEM. P values were determined by Student's t-test; ****P<0.0001.

Mice Lacking Mast Cells do not Experience Thrombocytopenia during Dengue Infection It has previously been shown that mast cell mediators contribute to plasma leakage during dengue infection [St John, A. L., et al., *eLife* 2, e00481 (2013); Syenina, A., et al., *eLife* 4, e05291 (2015)]. In the present example, C57BL/6 wild type (WT) and mast cell-deficient (Sash) mice (on a C57BL/6 background) were infected via the intraperitoneal route (IP) with $10^6$ plaque forming units (pfu) of DENV2. Blood was taken via cheek bleed 24 hours post-infection and platelet counts were measured using an automated hematology analyzer. Platelet counts in DENV-infected wild type (WT) and mast cell-deficient (Sash) mice indicated that mice that lacked mast cells (due to a point mutation in the promoter region of the ckit gene) did not experience the thrombocytopenia that occurred in control (WT) mice during dengue infection (FIG. 2).

Example 3

DENV2-Activated Mast Cells Induce Platelet Activation

Figure 3:
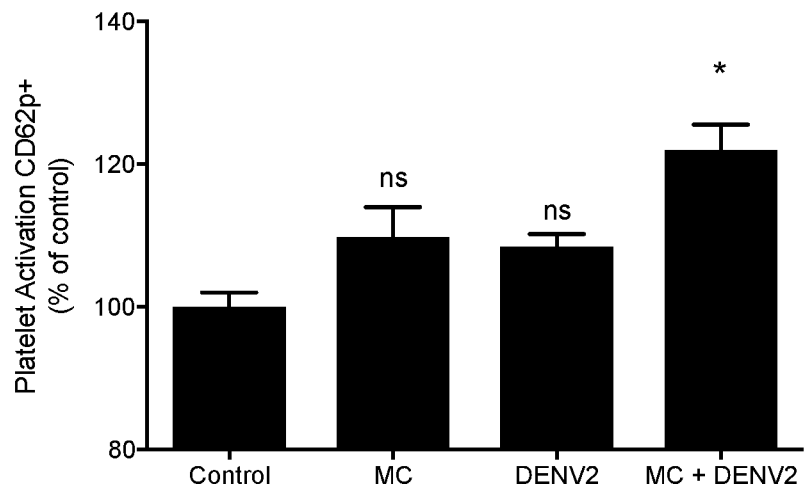
FIG. 3 shows that dengue induced mast cell degranulation products can activate platelets. Mouse bone marrow derived mast cells (MC) were incubated with DENV2 for 2 hours. Degranulation products were isolated and used to stimulate mouse whole blood. Samples were then analyzed through flow cytometry. Identification of activated platelets was done through the presence of the activation marker CD62P. Mast cells and DENV2 alone did not result in platelet activation while mast cell degranulation products following DENV2 stimulation did result in platelet activation (n=6 per group). Means are presented with error bars representing the SEM. P values were determined by one-way ANOVA; ns: non-significant, *P<0.05.

Further in vitro studies were undertaken to determine if mast cell products were able to directly activate platelets. Mouse bone marrow derived mast cells (MC) were incubated with DENV2 for 2 hours. Degranulation products were isolated and used to stimulate mouse whole blood. After 15 minutes, samples were fixed with 4% paraformaldehyde for 2 hours at 4 degrees. Samples were then washed and stained for platelet marker CD41 and activation marker CD62P and analyzed through flow cytometry. It can be seen that DENV2 alone and unstimulated mast cells did not result in significant levels of platelet activation. However, DENV2 activated mast cells released mediators that resulted in platelet activation (FIG. 3).

Example 4

Serotonin is Released from DENV-Activated Mast Cells

Figure 4:
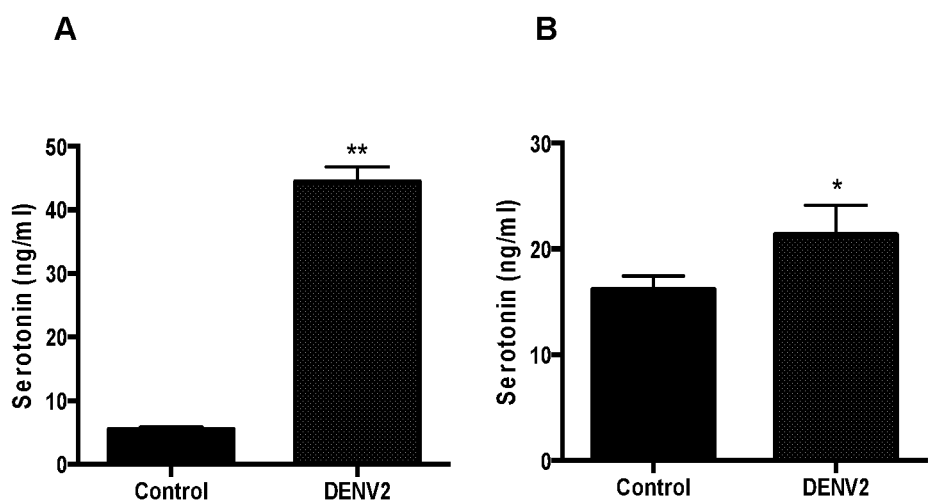
FIG. 4 shows that serotonin is released from DENV-activated mast cells. (A) The human mast cell line ROSA and (B) rat basophilic leukemic cells were activated with DENV at a multiplicity of infection (MOI) of 1. After 2 hours, supernatant was collected and ELISA was performed to measure serotonin release. DENV stimulation of mast cells significantly induced release of serotonin (n=2 per group). Means are presented with error bars representing the SEM. P values were determined by Student's t-test; * P<0.05, **P<0.01.

It has been understood for many years that serotonin, which is produced abundantly by mast cells [Sjoerdsma, A., et al., *Science* 125, 1202-1203 (1957)], can activate and aggregate platelets [Benedict, C. R., et al., *Circulation research* 58, 58-67 (1986); De Clerck. F. & Herman, A. *Federation proceedings* 1983, 228-232 (1983); Cerrito, E., et al., *Life sciences* 53, 209-215 (1993)]. Independently, it has also been shown that platelet activation is important for the subsequent dengue pathogenesis, through modulation of cytokine release [Hottz, E. D. et al., *The Journal of Immunology* 193, 1864-1872 (2014)]. Separately, it has been shown that one mechanism leading to platelet activation is via the serotonin receptor $5HT_{2A}$ and the downstream activation of the ERK pathway [Kurrasch-Orbaugh, D. M., et al., *Journal of Neurochemistry* 86, 980-991 (2003)]. The human mast cell line ROSA and rat basophilic leukemic cells were activated with DENV at a multiplicity of infection (MOI) of 1. After 2 hours, supernatant was collected and ELISA was performed to measure serotonin release. These findings demonstrate that both human and rodent mast cells release substantial amounts of serotonin when activated by DENV (FIGS. 4A and 4B, respectively).

Example 5

Ketanserin Treatment Blocks DENV-Induced Platelet Aggregation

Several studies have investigated the possibility of inhibiting the ERK pathway to block virus replication [Albarnaz, J. D. et al., *Antiviral Res* 111, 82-92 (2014)]; however, serotonin as a therapeutic target to block dengue replication or prevent platelet aggregation or thrombocytopenia during dengue infection has not been explored. One $5HT_{2A}$ receptor antagonist, ketanserin, is already in clinical use as an antihypertensive and has been shown to be able to affect platelet activation in vitro [de Clerck. F., David, J. L. & Janssen, *Agents Actions* 43, 225-234 (1994)]. In addition, ketanserin has other immune modulating effects (e.g. inhibiting NO synthase production) [Liu, C. et al., *J Infect Dis* 204, 1605-1612 (2011); Liu, C. et al., *Free Radic Biol Med* 65, 658-666 (2013)] that we propose could potentially also be beneficial for treating dengue fever. Serotonin receptor antagonists are also used for the treatment of nausea, particularly that induced by chemotherapy [Gregory, R. E. & Ettinger, D. S. *Drugs* 55, 173-189 (1998)]; thus, this might be another key symptom of dengue [Gubler, D. J. *Clinical microbiology reviews* 11, 480-496 (1998)] that could potentially be impacted by targeting serotonin.

Figure 5:
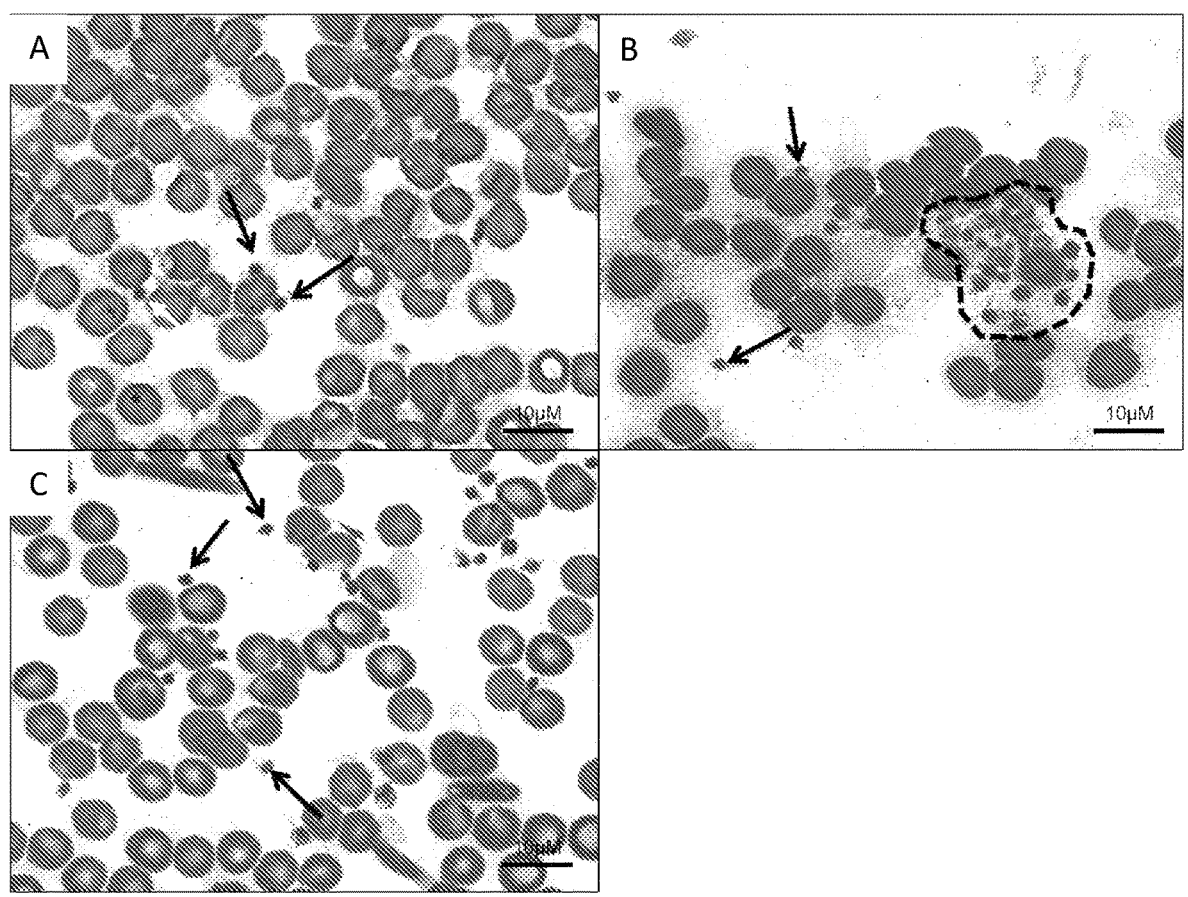
FIG. 5 shows that ketanserin treatment blocks platelet aggregation. Images depict peripheral blood smears from DENV2-infected mice. Mice were infected via intraperitoneal route (IP) with $10^6$ pfu. (A) Mock infected mice. (B) DENV-infected mice treated with vehicle control IP. (C) DENV-infected mice given ketanserin 8 mg/kg IP. Blood was taken via cheek bleed 24 hours post-infection, smeared onto glass slides, stained with eosin and methylene blue and viewed under light microscopy using a 100× magnification lens. Dengue induces platelet aggregation, while administration of ketanserin prevents this. A few individual platelets are indicated by arrows; platelet aggregates are circled by dashed lines. Scale bar=10 µm.

To test whether ketanserin could block platelet aggregation and/or prevent thrombocytopenia, a mouse model of dengue infection was used. WT mice were infected via intraperitoneal route (IP) with $10^6$ pfu of DENV2 and, after 1 hour, treated with vehicle (1% DMSO) or ketanserin (8 mg/kg) IP. Blood was taken via cheek bleed 24 hours post-infection, smeared onto glass slides, stained with eosin and methylene blue and viewed under light microscopy using a 100× magnification lens. FIG. 5 shows results for (A) Mock infected mice; (B) DENV-infected mice treated with vehicle control IP; and (C) DENV-infected mice given ketanserin (8 mg/kg) IP. Selected red blood cells (RBC), platelets (arrows) and platelet aggregates (dashed lines) are labeled. Results showed that Dengue infection induced platelet aggregation, while administration of ketanserin prevented this.

Example 6

Mast Cell Release of Serotonin Promotes Thrombocytopenia during DENV Infection

Figure 6:
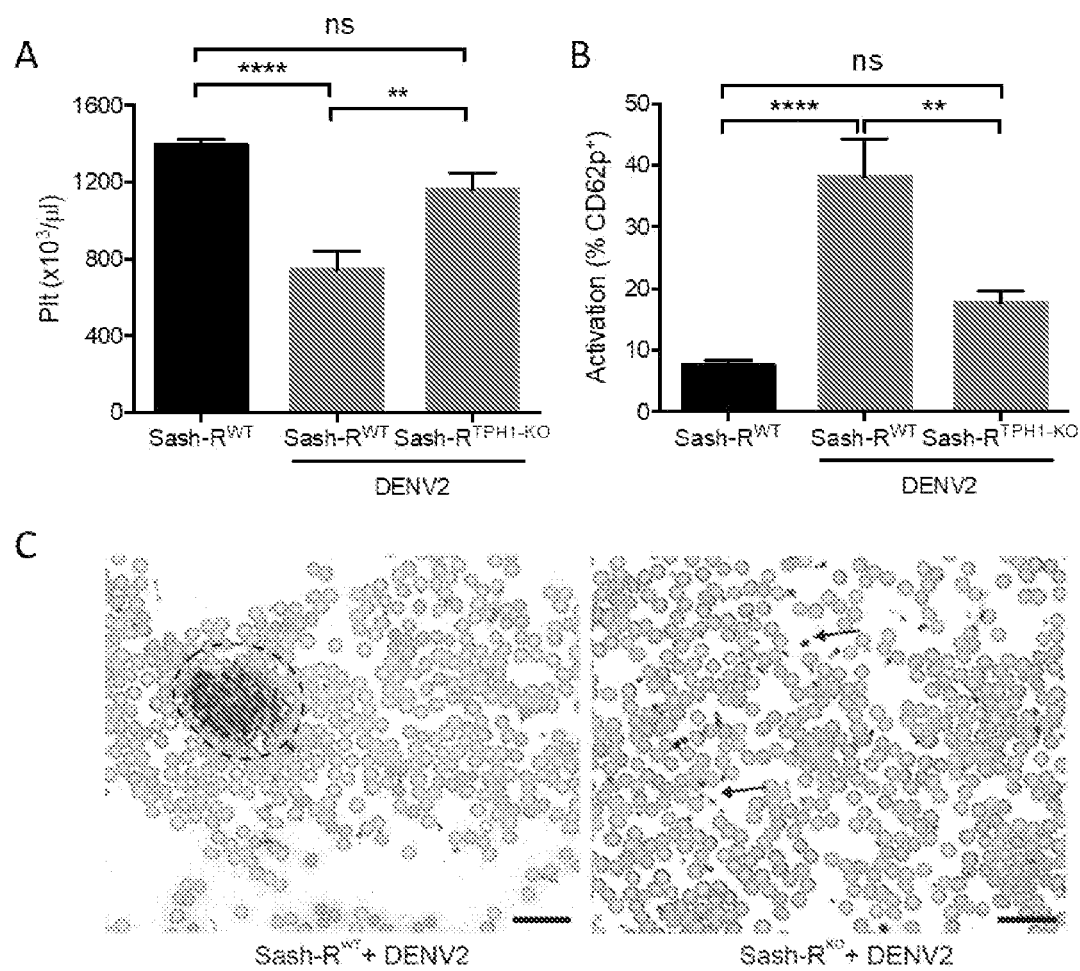
FIG. 6 shows that mast cell release of serotonin promotes thrombocytopenia during DENV infection. Mice selectively deficient in mast cell-serotonin were generated through reconstitution of Sash mice with bone marrow-derived mast cells (BMMCs) deficient in the enzyme TPH-1 (Sash-R$^{TPH1-KO}$) For controls, mice were reconstituted with BMMCs from WT mice (Sash-R$^{WT}$). (A) Platelet counts decreased significantly in Sash-R$^{WT}$ infected with DENV2 but not in infected Sash-R$^{TPH1-KO}$ mice at day 3 post infection (n=7-9 per group). (B) Increased numbers of activated platelets (CD41$^+$CD62P$^+$) were detected in the circulation of DENV-infected Sash-R$^{WT}$ mice but not in infected Sash-R$^{TPH1-KO}$ compared to uninfected controls (n=7-9 per group). (C) Representative eosin and methylene blue staining of peripheral blood smears day 3 post-infection. Some individual platelets are indicated by arrows. Platelet aggregates are surrounded by a dashed line. Scale bar=25 µm. Means are presented with error bars representing the SEM. P values were determined by one-way ANOVA; ns: non-significant,  P<0.01, *P<0.001.

To further support that serotonin from mast cells leads to DENV-induced thrombocytopenia, an alternative model of serotonin deficiency was explored. For this, mice specifically deficient in mast cell serotonin were generated (Sash-$R^{TPH1-KO}$), where the ability to synthesize serotonin was blocked only in the mast cells and not in other cell types. This involved reconstituting mice that were specifically deficient in mast cells due to a genetic deficiency (Sash mice) with bone marrow derived mast cells (BMMCs) that are either deficient in serotonin synthesis (Sash-$R^{TPH1-KO}$) or competent to produce serotonin (Sash-$R^{WT}$). Compared to mice with mast cell serotonin (Sash-$R^{WT}$), it was observed that the Sash-$R^{TPH1-KO}$ group had reduced thrombocytopenia following DENV infection (FIG. 6A). Sash-$R^{TPH1-KO}$ mice lacking mast cell-serotonin had reduced platelet activation (FIG. 6B), as shown by comparing the peripheral blood films of these mice. This revealed increased platelet aggregates in the blood of DENV-infected Sash-$R^{WT}$ mice, but not Sash-$R^{TPH1-KO}$ mice (FIG. 6C). These data demonstrate a clear requirement for mast cell serotonin production in order for DENV to be able to induce thrombocytopenia.

Example 7

Figure 7:
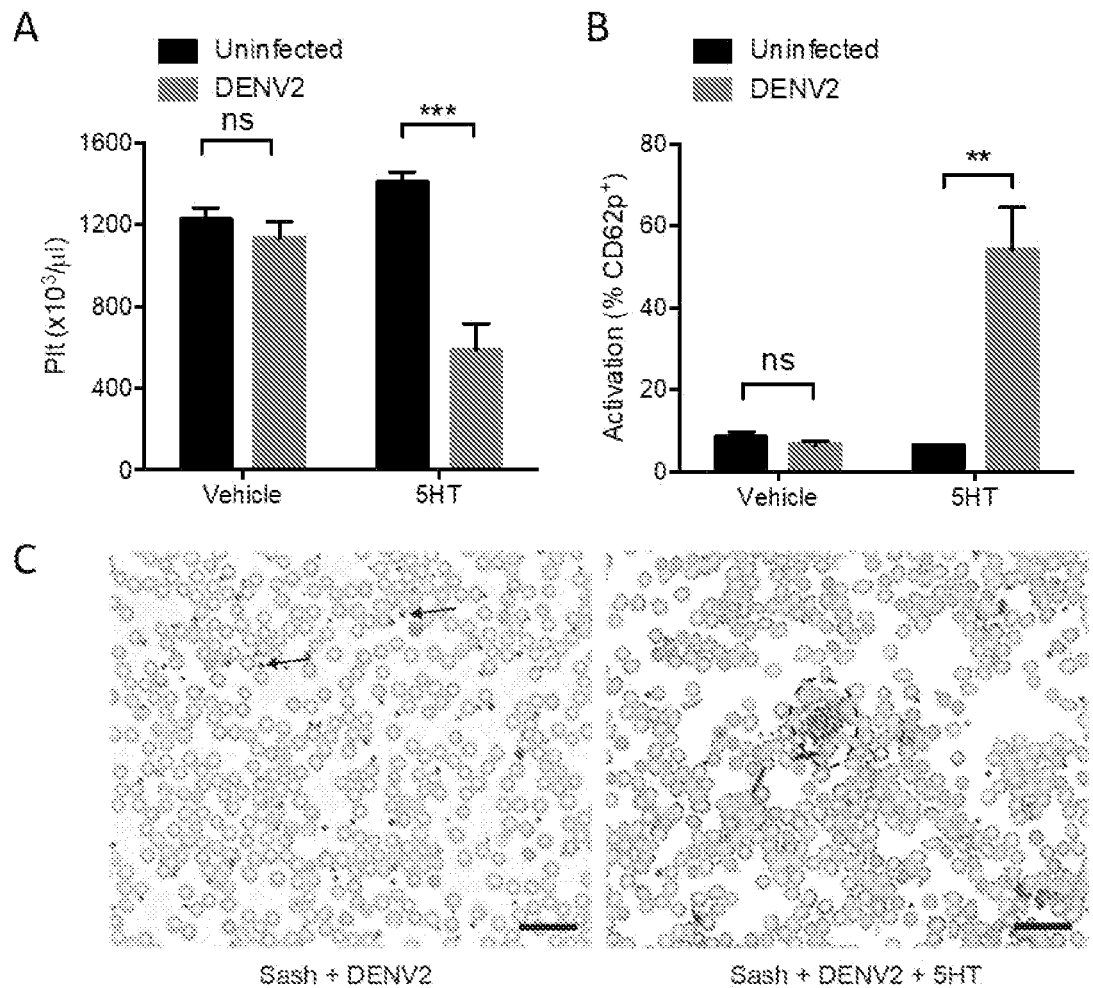
FIG. 7 shows exogenous serotonin restores the thrombocytopenic phenotype in DENV-infected mast cell-deficient mice. (A) Sash mice were infected with DENV2 and treated with 150 mg/kg of serotonin or vehicle daily. Blood was taken for analysis 3 days post-infection. In infected animals, treatment with serotonin significantly reduced circulating platelet counts compared to vehicle (mock)-treated animals. (B) Serotonin treatment resulted in increased platelet activation in infected mice compared to vehicle treated controls (n=5-8 per group). (C) Representative eosin and methylene blue staining of peripheral blood smears day 3 post-infection. Some individual platelets are indicated by arrows. Platelet aggregates are surrounded by a dashed line. Scale bar=25 µm. Means are presented with error bars representing the SEM. P values were determined by Student's unpaired t test; ns: non-significant, P<0.01, *P<0.001.

Exogenous Serotonin Restores the Thrombocytopenic Phenotype in DENV-Infected Mast Cell-Deficient Mice To provide another demonstration that the mechanism of thrombocytopenia during DENV infection is due to the serotonin pathway, which the present invention aims to inhibit, MC-deficient Sash mice were infected with DENV and treated with exogenous serotonin. Indeed, serotonin treatment restored the phenotypes of thrombocytopenia (FIG. 7A) and platelet activation (FIG. 7B) that were absent in Sash mice during DENV infection. The peripheral blood films of these mice revealed increased platelet aggregates in the blood of DENV-infected mice that were treated with serotonin, but not in blood from vehicle-treated mice (FIG.

7C). These results support that mast cells promote thrombocytopenia through the release of serotonin during DENV infection.

Example 8

Figure 8:
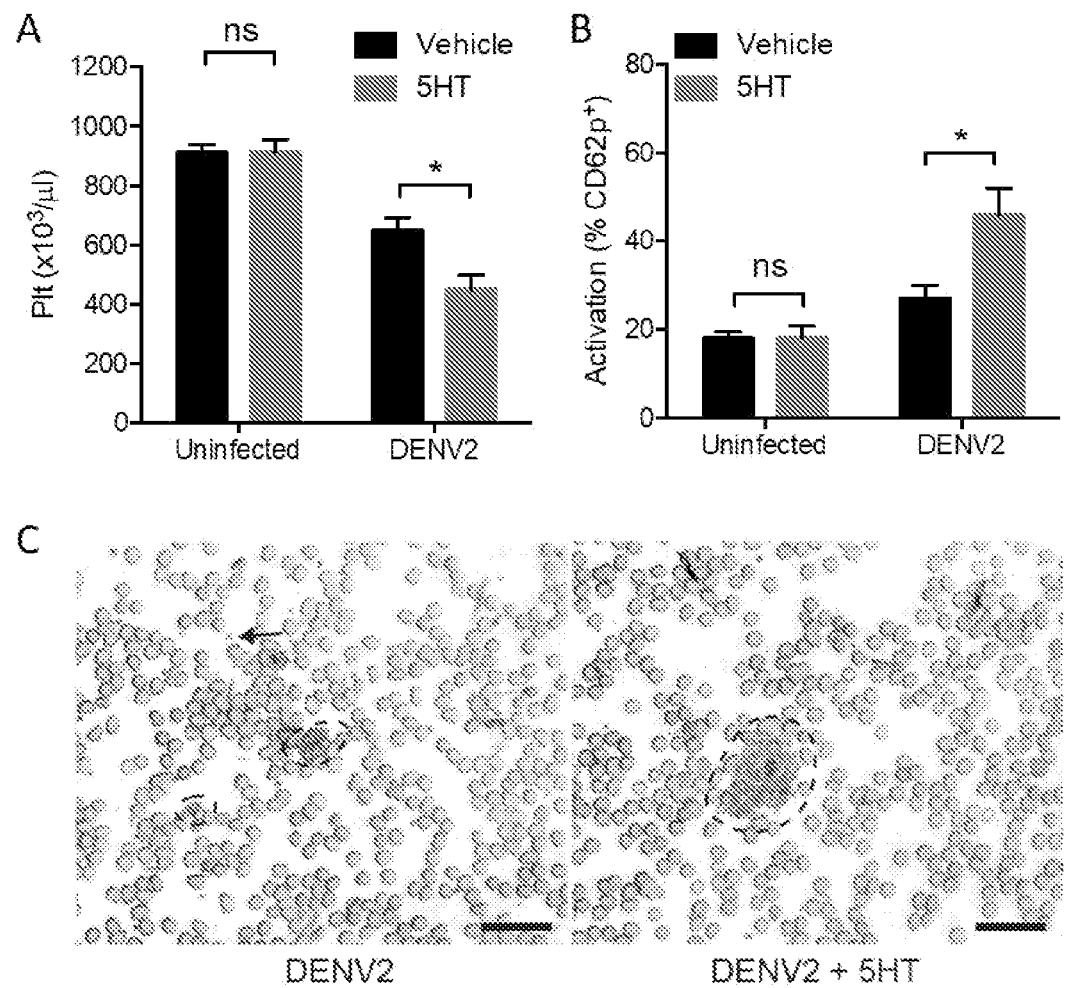
FIG. 8 shows exogenous serotonin worsens thrombocytopenia and increases platelet activation during DENV infection. (A) WT mice were infected with DENV2 (1×10$^6$ pfu i.p.) and treated with 150 mg/kg of serotonin or vehicle daily. Serotonin treatment did not affect platelet counts in uninfected WT mice. Serotonin treatment worsened thrombocytopenia during DENV infection compared to vehicle-treated mice, at 3 days post-infection. (B) Blood of DENV infected mice treated with serotonin or vehicle was isolated and stained for platelet marker CD41 and activation marker CD62P and analyzed by flow cytometry. Serotonin treatment did not result in platelet activation in uninfected mice. DENV infection resulted in increased platelet activation, which was further increased when mice were also treated with exogenous serotonin (n=6-12 per group). (C) Representative peripheral blood smears, day 3 post-infection, show platelet aggregation (dashed lines), which was more visually apparent following exogenous serotonin treatment compared to DENV infection. Some individual platelets are indicated by arrows. Scale bar=25 µm. Mean values are presented and error bars represent the SEM. P values were determined by Student's unpaired t test; *P<0.05, ns: non-significant.

Exogenous Serotonin Worsens Thrombocytopenia and Increases Platelet Activation during DENV Infection The release of mast cell products has been shown to correlate with DENV severity and herein serotonin was identified as a mast cell product contributing to thrombocytopenia. Of interest was whether increased mast cell activation and, hence, a greater release of mast cell serotonin, could worsen thrombocytopenia. WT mice were infected with DENV and administered exogenous serotonin to determine if there was an increase in platelet activation mediated by serotonin and if this would worsen thrombocytopenia in vivo. Platelet counts in serotonin-treated DENV-infected mice were lower (FIG. 8A), and the platelets showed increased activation (FIG. 8B). This was similarly observed in peripheral blood films, where platelet aggregates increased in serotonin-treated mice (FIG. 8C). These findings suggest that the increased release of serotonin from MCs could result in worse thrombocytopenia, further emphasizing the importance of therapeutically targeting this pathway.

Example 9

Figure 9:
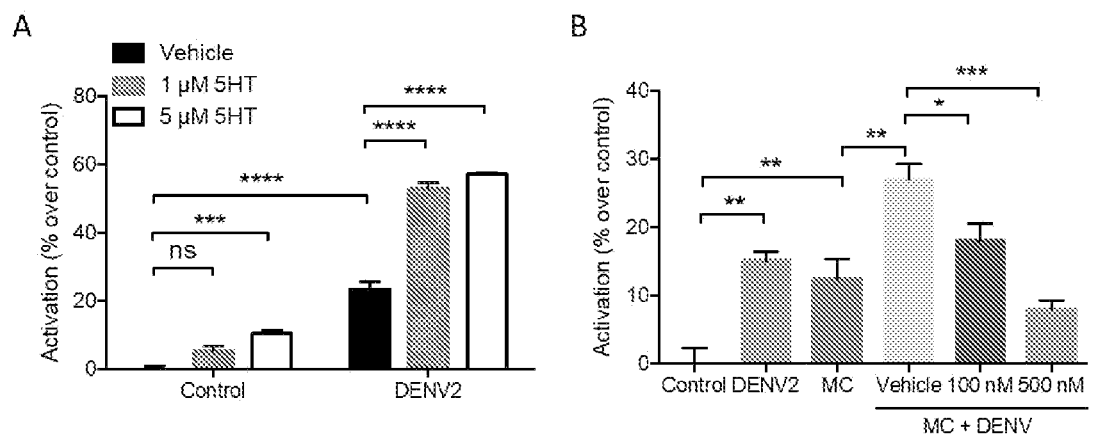
FIG. 9 shows serotonin exacerbates platelet activation in response to DENV in human platelets via 5HT$_{2A}$ receptors.

Serotonin Exacerbates Platelet Activation to DENV in Human Platelets via $5HT_{2A}$ Receptors To ensure that the findings were translatable to humans, whole blood from healthy volunteers was co-cultured with serotonin and there was observed an increase in activation of human platelets in response to DENV (FIG. 9A) as seen by an increase in $CD62P^+$ platelets. Additionally, products from DENV-stimulated human mast cells promoted platelet activation, dependent on platelet $5HT_{2A}$ receptor, since this effect was abolished by ketanserin (FIG. 9B). Thus, it was demonstrated that mast cell-serotonin triggers human platelet activation in response to DENV via the $5HT_{2A}$ receptor, suggesting that the findings herein are translatable to humans. Furthermore, ketanserin is effective in reversing DENV-induced human platelet activation.

Example 10

Ketanserin Treatment Prevents DENV-Induced Thrombocytopenia

WT mice were infected via intraperitoneal route (IP) with $10^6$ plaque forming units (pfu) of DENV2 and were given either vehicle (1% DMSO) or ketanserin (8 mg/kg) IP. Blood was taken via cheek bleed 24 hours post-infection and platelet counts were measured using an automated hematology analyzer. Results showed that DENV2 infection induced thrombocytopenia, whereas mice treated with ketanserin did not show significantly reduced platelets compared to control, vehicle-treated mice (*p<0.001, **p<0.0001) (FIG. 10).

Example 11

Ketanserin Treatment Prevents Thrombocytopenia in an Alternative Mouse Model of DENV To demonstrate our findings in another established DENV mouse model, we infected mice which were deficient in interferon signaling (IFNαβγ-KO). These mice are commonly used in the study of DENV as their deficiency in interferon signaling results in sustained DENV replication [St John, A. L., et al., *eLife* 2, e00481 (2013)]. IFNαβγ-KO mice were infected via the intraperitoneal route (IP) with $10^6$ plaque forming units (pfu) of DENV2 and were given either vehicle (1% DMSO) or ketanserin (8 mg/kg) IP once daily thereafter. Blood was taken via cheek bleed 24 and 72 hours post-infection and platelet counts were measured using an automated hematology analyzer. FIG. 11 shows that DENV2 infection with vehicle induced thrombocytopenia, but ketanserin treatment was able to maintain the initial normal platelet count (****p<0.0001).

Example 12

Targeting Serotonin Receptors Prevents Thrombocytopenia

One limitation of the experimental protocol in Examples 10 and 11 is that the vehicle used to deliver ketanserin in mice, DMSO, can itself interfere with platelet aggregation [Rosenblum, W. I. & El-Sabban. F. *Stroke* 13, 35-39 (1982)]. This difference can be observed by comparing the severity of thrombocytopenia in dengue-infected mice between FIGS. 1 and 10. Accordingly, newer serotonin receptor antagonists that are more soluble in saline were tested, to determine whether a similar effect is seen even without the confounding effects of DMSO. Mice were infected IP with $10^6$ pfu of DENV2 and were given either vehicle, the 5HT1A antagonist WAY-100135 (3 mg/kg), or one of the 5HT2A antagonists ketanserin (8 mg/kg) or sarpogrelate (3 mg/kg). Blood was taken via cheek bleed 24 hours post-infection and platelet counts were measured using an automated hematology analyzer. FIG. 12 shows that DENV2 infection induced thrombocytopenia, and that this could be prevented through administration of any of the three serotonin receptor antagonists tested.

Example 13

Targeting 5HT2A Receptors does not Affect Viremia During DENV Infection

Since a concern with inhibition of host factors would be the effect on viral replication, the levels of viremia following DENV infection were measured. WT mice were treated with either ketanserin or vehicle prior to a subcutaneous footpad injection. The draining lymph nodes were then harvested to determine if targeting $5HT_{2A}$ receptors had any influence on viral load. No difference in viral load was observed (FIG. 13A) in the lymph node, suggesting that serotonin did not play a role in the clearance of local infection. Subsequently it was determined whether targeting serotonin would have an effect on viral load in systemic infection. WT mice were treated with either ketanserin or vehicle following DENV systemic infection via intraperitoneal injection. Serum was isolated at days 1 and 3 post-infection and viremia quantified. There was no significant difference in serum DENV genome copy numbers at both time points in ketanserin-treated WT mice compared to vehicle-treated mice (FIG. 13B). This was further validated by looking at viral load in the spleen, which showed no difference between ketanserin and vehicle treated groups (FIG. 13C). The second model of severe DENV infection, the IFN-α,β,γ-R$^{-/-}$ (IFNR-KO) mice, were subsequently infected and treated with either ketanserin or vehicle. These mice are known to have higher levels of viremia than WT mice. Consistent with observations in WT mice, there was no difference in viral load between vehicle and ketanserin-treated mice 3 days post-infection in both the serum (FIG. 13D) and the spleen (FIG.

13E). This supports that the platelet $5HT_{2A}$ is likely to be a safe target for the treatment of thrombocytopenia since it specifically inhibits platelet activation and aggregation leading to thrombocytopenia, but does not amplify the virus infection.

Example 14

Ketanserin Reduces JEV Induced Thrombocytopenia

Japanese encephalitis virus (JEV) is a flavivirus related to dengue, so the ability of ketanserin to inhibit JEV-induced thrombocytopenia was also tested. Mice were infected with $10^6$ pfu of JEV IP, and were treated at 1 hour post-infection with vehicle (1% DMSO) or ketanserin (8 mg/kg). At 24 hours, blood was collected and platelet counts were measured. The reduction in platelet counts induced by JEV was inhibited by ketanserin treatment (FIG. 14).

Example 15

Fluoxetine Reduces DENV Induced Thrombocytopenia

Fluoxetine, an SSRI, prevents the uptake of serotonin into platelets. Activation of platelets by DENV (FIG. 3), will result in the release of stored serotonin, which can act in a positive feedback loop. Mice were treated with fluoxetine (20 mg/kg/day) or vehicle in drinking water for 2 weeks and infected with $10^6$ pfu of DENV IP. At 24 and 72 hours, blood was collected and platelet counts were measured. The reduction in platelet counts and increased platelet activation induced by DENV was inhibited by fluoxetine treatment (FIG. 15).

Example 16

Schematic Diagram of the Targets of the Invention

DENV activates mast cells, leading to their degranulation and the release of serotonin (FIG. 16 #1). Serotonin acts on mast cells via 5-HT1A receptors in an autocrine manner, further increasing release of mast cell-derived products (FIG. 16 #2). Serotonin acts on platelets via the 5HT2A receptor (FIG. 16 #3), leading to platelet aggregation and subsequently thrombocytopenia (FIG. 16 #4) which is restored during recovery as new platelets are released from the bone marrow (FIG. 16 #5). Possible pharmacological inhibitors of these receptors are shown as WAY 100-135, ketanserin and sarpogrelate.

The data presented herein has demonstrated that serotonin contributes to thrombocytopenia. Apart from acting on 5HT2A receptors on platelets, serotonin can act via serotonylation of platelet proteins to increase platelet activation [Walther, D. J., et al. Cell 115, 851-62 (2003)]. Therefore, serotonylation represents another target for therapy, though no approved drugs are yet available to target this pathway. We predict that use of a serotonylation inhibitor, such as cystamine, would reduce the activation of platelets in response to DENV and serotonin.

Serotonin in platelets represents a mechanism for which positive feedback can worsen thrombocytopenia. Activation of platelets during infection leads to release of serotonin stores from the platelets themselves. It has been shown that this second-wave of serotonin can act on other platelets and increase their activation further as has been demonstrated. Hence, we propose another potential target to prevent virus-induced thrombocytopenia would be to block the accumulation of serotonin by platelets. This can be done by antagonists of the serotonin transporter on platelets, such as with selective serotonin uptake inhibitors (SSRIs) or with serotonin antagonist and reuptake inhibitors (SARIs) [Omer, I., et al. Blood 112, 4556 (2008)]. Examples of such drugs include fluoxetine, paroxetine, citalopram, etoperidone and lorpiprazole.

Apart from individual targets, we propose using a combination treatment for thrombocytopenia. This can involve targeting mast cell release of serotonin, such as with mast cell stabilizers or $5HT_{1A}$ antagonists, together with blocking platelet $5HT_{2A}$ receptors with antagonists. We predict that combinations of drugs targeting multiple aspects of the serotonin pathway could have a synergistic or additive effect, further reducing thrombocytopenia, and also potentially having fewer side effects due to lower levels of drugs needed to be used.

SUMMARY

Importantly, whilst the mechanism of dengue-induced thrombocytopenia is not known, the studies herein have identified serotonin as a critical factor promoting thrombocytopenia during dengue infection, making this pathway a novel therapeutic target (FIGS. 5-12).

The approach used herein involves infecting mice with DENV and observing the effect of a serotonergic drug on a characteristic symptom of dengue disease, in particular, thrombocytopenia but also platelet activation and aggregation. As seen in FIG. 5, dengue infection induced platelet aggregation, while ketanserin treatment prevented this. DENV2 infection also induced thrombocytopenia, which ketanserin or sarpogrelate treatment prevented (FIGS. 10, 11 and 12). Taken together, this set of data supports the use of serotonergic drugs, such as ketanserin, in the treatment of dengue fever.

Since we propose that mast cells release serotonin, resulting in platelet activation, we also aimed to block upstream of platelet activation, by reducing mast cell release of serotonin. Targeting the mast cell 5HT1A receptor with WAY100135 also inhibited thrombocytopenia (FIG. 12). The results have highlighted that targeting upstream of platelet activation, via reducing release of serotonin from mast cells is also beneficial, in addition to the downstream effect of directly inhibiting platelet serotonin receptors (FIG. 12).

Platelets can release serotonin upon activation, resulting in a positive feedback loop. Reducing platelet serotonin by preventing uptake using SSRIs such as fluoxetine blocks this feedback loop reducing thrombocytopenia (FIG. 15).

It would be understood that there are several alternative drugs to target the serotonin 5HT2A receptor and/or the serotonin 5HT1A receptor. Apart from ketanserin, other drug choices include sarpogrelate, ritanserin, fananserin or antipsychotics, such as risperidone or quitiapine. An alternative to WAY 100135 includes antagonists such as methiothepin, pindolol, dotarizine and flopropione. An alternative to fluoxetine includes paroxetine, citalopram, etoperidone and lorpiprazole.

Another alternative is to target further downstream of the serotonin activation pathway, via ERK pathway inhibitors, such as SCH772984 and VTX11e. Other inhibitors of pathways involved in platelet activation, such as those targeting platelet glycoprotein IIb/IIIa or the adenosine receptor could be utilized. Since mast cells serve as the primary source of serotonin outside of the central nervous system, using mast cell stabilizers such as cromolyn and ketotifen (as has previously been proposed [Soman N. A. & St. John A. L.

Patent Application PCT/US2013/032553)]) represents an alternative way to limit serotonin release, but by an alternative strategy.

REFERENCES

Any listing or discussion of an apparently prior-published document in this specification should not necessarily be taken as an acknowledgement that such document is part of the state of the art or is common general knowledge.
1. Albarnaz, J. D. et al. MEK/ERK activation plays a decisive role in yellow fever virus replication: implication as an antiviral therapeutic target. *Antiviral Res* 111, 82-92 (2014).
2. Assinger, A. Platelets and infection—An emerging role of platelets in viral infection. *Frontiers in immunology* 5, 649 (2014).
3. Benedict, C. R., Mathew, B., Rex, K. A., Cartwright, J. & Sordahl, L. A. Correlation of plasma serotonin changes with platelet aggregation in an in vivo dog model of spontaneous occlusive coronary thrombus formation. *Circulation research* 58, 58-67 (1986).
4. Cerrito, F., Lazzaro, M., Gaudio, E., Arminio, P. & Aloisi, G. 5HT 2-receptors and serotonin release: their role in human platelet aggregation. *Life sciences* 53, 209-215 (1993).
5. De Clerck. F. & Herman, A. 5-hydroxytryptamine and platelet aggregation. *Federation proceedings* 1983; 1983. p. 228-232.
6. de Clerck. F., David, J. L. & Janssen, P. A. Inhibition of 5-hydroxytryptamine-induced and-amplified human platelet aggregation by ketanserin (R 41,468), a selective 5-HT2-receptor antagonist. 1982. *Agents Actions* 43, 225-234 (1994).
7. Gregory, R. E. & Ettinger, D. S. 5-HT3 receptor antagonists for the prevention of chemotherapy-induced nausea and vomiting. A comparison of their pharmacology and clinical efficacy. *Drugs* 55, 173-189 (1998).
8. Gubler, D. J. Dengue and dengue hemorrhagic fever. *Clinical microbiology reviews* 11, 480-496 (1998).
9. Guzman, M. G. & Harris, E. Dengue. *The Lancet* 385, 453-465 (2015).
10. Halstead, S. B. Dengue. *Lancet* 370, 1644-1652 (2007).
11. Hottz, E. D. et al. Platelet activation and apoptosis modulate monocyte inflammatory responses in dengue. *The Journal of Immunology* 193, 1864-1872 (2014).
12. Kurrasch-Orbaugh, D. M., Parrish, J. C., Watts, V. J. & Nichols, D. E. A complex signaling cascade links the serotonin2A receptor to phospholipase A2 activation: the involvement of MAP kinases. *Journal of neurochemistry* 86, 980-991 (2003).
13. Langer, R, New methods of drug delivery. *Science* 249, 1527-1533 (1990).
14. Liu, C. et al. Effects of ketanserin on endotoxic shock and baroreflex function in rodents. *J Infect Dis* 204, 1605-1612 (2011).
15. Liu, C. et al. The protective action of ketanserin against lipopolysaccharide-induced shock in mice is mediated by inhibiting inducible NO synthase expression via the MEK/ERK pathway. *Free Radic Biol Med* 65, 658-666 (2013).
16. Omer, I., et al. Selective Serotonin Reuptake Inhibitors Influence Agonist-Induced Platelet Aggregation. Preliminary Results from Comorbidity of Depression and Cardiovascular Disease Study. *Blood* 112, 4556 (2008).
17. Remington *The Science and Practice of Pharmacy*, 19th ed., Mack Printing Company, Easton, Pa. (1995).
18. Rosenblum, W. I. & El-Sabban. F. Dimethyl sulfoxide (DMSO) and glycerol, hydroxyl radical scavengers, impair platelet aggregation within and eliminate the accompanying vasodilation of, injured mouse pial arterioles. *Stroke* 13, 35-39 (1982).
19. Sambrook and Russel, Molecular Cloning: A Laboratory Manual, Cold Springs Harbor Laboratory, New York (2001).
20. Sjoerdsma, A., Waalkes, T. P. & Weissbach. H. Serotonin and histamine in mast cells. *Science* 125, 1202-1203 (1957).
21. Soman N. Abraham & ST. JOHN Ashley L. Compositions and methods for the prevention and treatment of mast cell-induced vascular leakage 2013. 2013. (Patent Application PCT/US2013/032553)
22. St John, A. L., Abraham, S. N. & Gubler, D. J. Barriers to preclinical investigations of anti-dengue immunity and dengue pathogenesis. *Nature reviews. Microbiology* 11, 420-426 (2013).
23. St John, A. L., Rathore, A. P., Raghavan, B., Ng, M. L. & Abraham, S. N. Contributions of mast cells and vasoactive products, leukotrienes and chymase, to dengue virus-induced vascular leakage. *eLife* 2, e00481 (2013).
24. Syenina, A., Jagaraj, C. J., Aman, S. A., Sridharan, A. & St John, A. L. Dengue vascular leakage is augmented by mast cell degranulation mediated by immunoglobulin Fcγ receptors. *Elife* 4, e05291 (2015).
25. Walther, D. J., et al. Serotonylation of small GTPases is a signal transduction pathway that triggers platelet alpha-granule release. *Cell* 115, 851-62 (2003).

The invention claimed is:
1. A method of treatment of virus-induced thrombocytopenia, comprising administering to a subject in need thereof an efficacious amount of a composition comprising at least one serotonergic compound, a pharmaceutically acceptable salt, or a solvate thereof, wherein the at least one serotonergic compound is at least one serotonin 5HT2A receptor inhibitor and/or at least one serotonin 5HT1A receptor inhibitor.
2. The method of claim 1, wherein
the at least one 5HT2A receptor inhibitor is selected from the group consisting of
[3-[2-[4-(4-fluorobenzoyl)piperidin-1-yl]ethyl]-1H-quinazoline-2,4-dione] (ketanserin),
[4-[1-(dimethylamino)-3-[2-[2-(3-methoxyphenyl)ethyl]phenoxy]propan-2-yl]oxy-4-oxobutanoic acid] (sarpogrelate),
[6-[2-[4-[bis(4-fluorophenyl)methylidene]piperidin-1-yl]ethyl]-7-methyl-[1,3]thiazolo[3,2-a]pyrimidin-5-one] (ritanserin), and
[2-(3-(4-(4-fluorophenyl)-1-piperazinyl)propyl)-2H-naphth(1,8-cd)isothiazole 1,1-dioxide] (fananserin); and/or
the at least one 5HT1A receptor inhibitor is selected from the group consisting of
[(S)—N-tert-butyl-3-(4-(2-methoxyphenyl)-piperazin-1-yl)-2-phenylpropanamide] (WAY 100135),
[1-methyl-4-(3-methylsulfanyl-5,6-dihydrobenzo[b][1]benzothiepin-5-yl)piperazine] (methiothepin),
[1-(1H-indol-4-yloxy)-3-(propan-2-ylamino)propan-2-ol] (pindolol),
[1-(Diphenylmethyl)-4-[3-(2-phenyl-1,3-dioxolan-2-yl)propyl]piperazine] (dotarizine), and
[1-(2,4,6-Trihydroxyphenyl)-1-propanone] (flopropione).

3. The method of claim 1, wherein the at least one serotonergic compound is selected from the group consisting of ketanserin, sarpogrelate, and WAY 100135.

4. The method of claim 1, wherein the composition is administered orally, sublingually, intravenously or intraperitoneally.

5. The method of claim 1, wherein the virus is selected from the group consisting of a flavivirus, human immunodeficiency virus, hepatitis C, bunyaviruses, rotavirus, hantavirus, adenovirus, Epstein-Barr virus, and cytomegalovirus.

6. The method of claim 1, wherein the virus is a flavivirus.

7. The method of claim 1, wherein the virus is dengue virus or Japanese encephalitis virus.

8. A method of treatment of virus-induced thrombocytopenia, comprising administering to a subject in need thereof an efficacious amount of a composition comprising at least one serotonergic compound, a pharmaceutically acceptable salt, or a solvate thereof, wherein the at least one serotonergic compound is an antipsychotic, an ERK pathway inhibitor, cystamine, a selective serotonin uptake inhibitor (SSRI), or an serotonin antagonist and reuptake inhibitor (SARI).

9. The method claim 8, wherein the antipsychotic is selected from the group consisting of

[3-[2-[4-(6-fluoro-1,2-benzoxazol-3-yl)piperidin-1-yl] ethyl]-2-methyl-6,7,8,9-tetrahydropyrido[1,2-a]pyrimidin-4-one] (risperidone) and

[2-[2-(4-benzo[b][1,4]benzothiazepin-6-ylpiperazin-1-yl) ethoxy]ethanol] (quetiapine).

10. The method of claim 8, wherein the ERK pathway inhibitor is selected from the group consisting of

[(3R)-1-[2-oxo-2-[4-(4-pyrimidin-2-ylphenyl)piperazin-1-yl]ethyl]-N-(3-pyridin-4-yl-1H-indazol-5-yl)pyrrolidine-3-carboxamide] (SCH772984) and

[4-[2-(2-chloro-4-fluoroanilino)-5-methylpyrimidin-4-yl]-N-[(1S)-1-(3-chlorophenyl)-2-hydroxyethyl]-1H-pyrrole-2-carboxamide] (VTX11e).

11. The method of claim 8, wherein the at least one serotonergic compound is selected from the group consisting of fluoxetine, paroxetine, citalopram, etoperidone, and lorpiprazole.

12. The method of claim 8, wherein the composition is administered orally, sublingually, intravenously or intraperitoneally.

13. The method of claim 8, wherein the virus is selected from the group consisting of a flavivirus, human immunodeficiency virus, hepatitis C, bunyaviruses, rotavirus, hantavirus, adenovirus, Epstein-Barr virus, and cytomegalovirus.

14. The method of claim 8, wherein the virus is a flavivirus.

15. The method of claim 8, wherein the virus is dengue virus or Japanese encephalitis virus.

* * * * *